United States Patent [19]
Carter

[11] Patent Number: 6,099,304
[45] Date of Patent: Aug. 8, 2000

[54] INTRAORAL GROWTH APPLIANCE

[76] Inventor: David D. Carter, 3814 Shoal Creek Ct., Augusta, Ga. 30907

[21] Appl. No.: 09/400,584

[22] Filed: Sep. 22, 1999

[51] Int. Cl.[7] ........................................................ A61C 3/00
[52] U.S. Cl. .................................................................. 433/19
[58] Field of Search ................................... 433/18, 19, 24

[56] References Cited

U.S. PATENT DOCUMENTS

| | | | |
|---|---|---|---|
| 5,443,384 | 8/1995 | Franseen et al. | 433/19 X |
| 5,848,891 | 12/1998 | Eckhart et al. | 433/19 |
| 5,957,686 | 12/1998 | Anthony | 433/19 |

*Primary Examiner*—Nicholas D. Lucchesi
*Attorney, Agent, or Firm*—Todd Deveau; Ryan Schneider; Troutman Sanders LLP

[57] ABSTRACT

The present invention is a method and intraoral appliance for correcting malocclusions, incorporating an adjustment assembly and a placement assembly. The adjustment assembly is mounted to a tooth of the maxilla, and the placement assembly is mounted to a corresponding tooth of the mandible. The adjustment assembly cooperates with the placement assembly when the jaws are drawn together, in order to correct the patient's malocclusion. The amount of correction to the malocclusion is finely, continuously adjustable through the adjustment assembly. The adjustment assembly includes a first tooth attachment for mounting the adjustment assembly to a tooth on the maxillary jaw, an adjusting mechanism to lengthen or shorten the distance of forward positioning imparted to the patient's mandibular jaw, an abutment member to preserve the proper forward-moving force once the patient's jaws are properly closed, and an inhibiting member that inhibits the patient from closing his/her mouth unless the jaws are properly seated relative to one another as defined by the appliance settings. The placement assembly includes a second tooth attachment for mounting the placement assembly to a tooth on the mandibular jaw and a projection element extending from the second tooth attachment. The projection element has a stop end capable both of engagement with the inhibiting member of the adjustment assembly when the patient's jaws are not properly seated, and engagement with the abutment member of the adjustment assembly when the jaws are properly closed.

23 Claims, 4 Drawing Sheets

INTRAORAL GROWTH APPLIANCE

BACKGROUND OF THE INVENTION

1. Field of the Invention

This invention relates to an appliance and method for correcting a patient's malocclusion by encouraging relative jaw displacement, and more particularly, to an adjustable intraoral appliance that can deter an uncorrected bite, yet maintain a corrected bite.

2. Description of Related Art

Malocclusions are the improper positioning of the teeth and jaws. Generally, they are variations of the normal growth and development of the teeth and jaws that can affect a patient's bite, the ability to clean the teeth properly, gum tissue health, jaw growth, speech development and facial appearance. A bad bite can lead to a variety of problems, including abnormal wear of tooth surfaces, difficulty in chewing and excess stress on the supporting bone and gum tissue. Both heredity and environmental factors can play a role in the development of malocclusions. Some hereditary factors include the size and shape of the teeth and jaws, crowding of teeth, too much space between teeth, extra or missing teeth and cleft palate. Some environmental factors include tongue thrusting, dental disease and accidents, and habits like pacifier and finger/thumb sucking.

Malocclusions are categorized according to a class system. In Class I malocclusions, the jaws line up properly, but the teeth are crooked. Teeth are usually crowded, rotated and/or overlapped, and often are blocked out from alignment. In Class II malocclusions, the upper jaw appears to extend too far over the lower jaw. The lower or mandibular jaw bites in a retrusive position relative to the top or maxillary jaw. This misalignment is referred commonly as "buck" teeth, and more formally as overbite or overjet. Class III malocclusions are the opposite of Class II malocclusions; the lower jaw juts out further than the upper jaw, causing an underbite.

One of the problems encountered with a patient having a retrusive lower jaw (Class II malocclusion) is that the teeth of the lower jaw bite posterior to their normal correct biting positions against the upper teeth. Orthodontists have used a number of different devices over the years in an attempt to correct Class II malocclusions, including devices to hold the lower jaw forward from its retrusive position. After a period of time of wearing such a device, the bite hopefully becomes stable with the mandibular jaw in an advanced, "normal" position. This change is due both to migration of the teeth within the jaws, and to differential growth and remodeling of the jaws caused by wearing the device. In the field of orthodontics, a "normal" bite exists when the upper canine teeth bite distally relative to the lower canines, and the upper first molar mesial buccal cusp bites in the buccal groove between the lower first molar mesial and middle buccal cusps.

One approach to correct the overbite malocclusion is to wear an extraoral device, or headgear, which attaches via a face bow or j-hooks to the upper teeth by braces. The extraoral device exerts a force to the top or back of the head or the back of the neck through a tension device. This force, in turn, applies a posteriorly directed force to the upper teeth and jaw. Although such headgear offers one approach to correcting overbite or overjet, the device has several limitations. For example, because headgear is an extraoral device, it is highly visible and therefore has little patient appeal. Further, although headgear may be permanently attached, it usually is removable, and therefore, it often is difficult to ensure patient compliance.

Intraoral devices are also used to correct overbite. Intraoral devices overcome some of the disadvantages associated with extraoral devices. Some intraoral devices work exclusively on the teeth in the upper jaw, using the palate as an anchor. Other devices also can provide a posteriorly directed force to the upper jaw. Specific examples of such intraoral devices include the Jones jig and the Hilgers pendulum.

There are known other intraoral devices that attempt to correct overbite by both holding the lower jaw forward and tipping the upper jaw backward, while also moving the teeth in both jaws toward a corrected position. These devices apply both posteriorly directed forces to the upper teeth and jaw, and anteriorly directed forces to the lower teeth and jaw. Examples of such devices include Class II elastics, activators, bionators, Frankels, removable Herbsts, twin blocks and Korn appliances. Yet, these intraoral appliances are removable, limiting the effectiveness of such devices, similar to the external appliances, because of patient non-compliance.

Non-removable intraoral devices exist, which devices are permanently attached in the mouth. Specific examples of such permanent appliances include SAIF springs, Jasper jumpers, mandibulators and Herbst appliances. One of the limitations of this group of non-removable devices is that each of these devices creates some sort of permanent connection between the upper and lower teeth. Various types of linkages are used so that during natural closing and opening movements of the patient's jaws during speaking and chewing, the lower jaw is forced into an improved, forward position with respect to the upper jaw. The opening or closing forces of the jaw muscles are thus utilized to bring about the desired correction. A permanent change in the positional relationship of the jawbones occurs with use of such devices; therefore, this practice is termed "dental orthopedics". Some appliances for this purpose have employed rubber bands or springs arranged so that opening of the mouth tends to draw the lower jaw forward. Another approach to permanent appliances is the use of telescoping but rigid linkages between the upper and lower jaws that push the latter forward when the mouth is closed. Among other problems, this type of permanent connection appliance inhibits lateral jaw movement. During the months that the patient must wear this type of appliance, there are numerous occasions when side to side movement must be made. Any limitation of this mobility increases the discomfort of wearing the appliance.

Orthotic devices also are used in fields other than malocclusion correction, for example, in cases of temporomandibular joint (TMJ) dysfunction in order to advance the lower jaw for relief of pain, or to reduce clicking or locking. It is believed that such devices provide relief by decompressing the posterior ligaments of the condyle disk, by reducing the ability to clench the jaw-closing muscles when the lower jaw is forward, and by "recapturing" the displaced condyle disk onto the head of the condyle of the lower jaw. Devices currently being used to treat TMJ include a plastic orthotic portion or portions attached to the teeth and jaw with plastic indices attached to the opposing teeth so as to hold the lower jaw open and forward. However, such devices have several limitations, including that they are relatively bulky and do not allow the teeth of both jaws to be moved orthodontically while holding the lower jaw forward.

Additionally, orthodontic or orthopedic devices are used in the field of sleep disorders, for example, to treat snoring or obstructive sleep apnea. In the sleep disorder arena, it is known that snoring and obstructive sleep apnea usually are due, at least in part, to the tongue falling posteriorly during sleep, thereby pressing on the soft palate and reducing or blocking the airway. Traditional anti-snoring dental devices employ the principle of holding the lower jaw forward, thereby keeping the tongue out of the throat during sleep. Examples of such devices include bionators, activators, Herbsts and Jasper jumpers as mentioned above, as well as other devices such as the Snoreguard, SNOAR, NAPA, ASD and Feldman/Shapiro appliances. Although these devices usually offer some relief in the treatment of snoring or obstructive sleep apnea, they also include several disadvantages. For example, these devices are removable, raising patient compliance problems. In addition, several of the appliances are quite bulky. Further, many of the appliances result in morning jaw stiffness. Finally, these devices are difficult to wear if the teeth are being moved orthodontically.

Some specific examples of prior art references disclosing appliances addressed above include U.S. Pat. No. 4,382,783 to Rosenberg. Rosenberg discloses a linkage device used to join an upper molar and a lower molar on both sides of the mouth. An upper link 4 is hingedly attached at one end to a mounting block 3 extending from an upper molar, and hingedly attached at the other end to a cylinder 9 and a piston 5, which both serve as the lower link, attached to a lower molar mounting block. The linkage assembly of Rosenberg permanently links the maxillary and mandibular bones during use of the device. Rosenberg further discloses adjusting mechanisms including use of a spring 20 (FIG. 9), and the increase or decrease in the length of the lower link utilizing a piston 5 incorporating a stop 50, a threaded portion 52, and lock nut 48. (FIGS. 10 and 11)

U.S. Pat. No. 4,795,342 to Jones discloses a spring module orthodontic device having telescoping members for use in repositioning teeth. U.S. Pat. No. 4,969,822 to Summer discloses a telescopic oral orthopedic appliance comprising upper and lower channel-shaped attachment members 20, 22, connected to one another by a cylindrical sleeve 80 with rods 90, 92 extending therefrom, which rods 90, 92 hook to the upper and lower attachment members 20, 22, respectively. U.S. Pat. No. 5,352,116 to West discloses an adjustable bite corrector that is stretchable and has a degree of flexibility.

Of particular relevance in relation to the present invention, U.S. Pat. No. 5,848,891 (the "'891 device") to Eckhart et al. discloses an intraoral mandibular anterior repositioning appliance, commonly referred to as the MARA device. FIG. 1 of Eckhart et al. shows a typical overbite situation wherein the top jaw extends a distance x from the lower jaw. When the '891 device is installed in the patient's mouth, and the wearer attempts to close his/her mouth without properjaw adjustment, an abutment surface 60 of an L-shaped obstruction element 16 extends from a first member 12 attached to the patient's upper jaw, and rests atop an extending projection 24 connected to his/her lower jaw. As FIG. 1 of Eckhart et al. shows, the patient cannot close his or her mouth without properly aligning the jaws because at a point 66, the abutment surface 60 rests atop projection 24. As shown in Eckhart et al. in FIG. 2, the patient can only close his/her mouth when the bottom jaw slides forward relative to the top jaw so that the obstruction element 16 clears projection 24.

The MARA device embodies limitations that curtail its application in a number of situations. Its limitations are outlined in a widely distributed and respected manual specifically written for orthodontists and staff that install the MARA device in the patients' mouths. The manual, Clinical Management of the MARA, ("CMM"), includes an acknowledgment to Dr. Jim Eckhart, the inventor of the '891 device, for his significant contributions to the manual. The CMM exhaustively describes the preferred fitting procedures for the MARA device, and intermittently notes its limitations.

One disadvantage of the MARA device is that upon its initial fitting within the patient's mouth, the lower jaw is immediately repositioned forward relative the upper jaw. CMM, page 5. The patient is not provided with an accommodation period to become comfortable with weight and feel of the MARA itself, without any adjustment to the positioning of the jaws. Yet, this immediate dislocation of the jaws creates discomfort for the wearer, as he/she has no time to adjust to the MARA device alone (as a foreign device in the mouth), without the further unpleasantness associated with the shifted lower jaw. Presumably, the patient has had the malocclusion for some time, if not all his/her life, so the immediate jaw adjustment forced upon them by the MARA device is quite unnatural. It would be beneficial to provide an intraoral device and method that is designed to provide the patient a time to accommodate the new appliance, without any initial adjustment to the patient's jaws.

Further, the MARA device has only limited, discrete adjustment settings. For example, if a patient has a 12 mm overbite or overjet, the MARA device may only incorporate three adjustment settings, initially thrusting the lower jaw forward 4 mm, then after some time another 4 mm, and finally the last 4 mm. "A medium 4–5 mm Class II can be advanced the entire 4–5 mm initially. A severe 8–9 mm Class II should be advanced halfway (4–5 mm) at first." CMM, page 11. Even though it may not seem like a 4–5 mm distance is perceptible, any MARA user will readily admit each 4 mm adjustment alone is painful, much less several such adjustments.

The embodiment of the MARA device shown in FIGS. 1 and 2 of Eckhart et al. in fact provides no adjustment capability whatsoever, wherein the bottom jaw is forced to thrust forward until obstruction element 16 clears projection 24, and the malocclusion is fully corrected upon the initial fitting of the device, regardless how far the lower jaw must be thrust forward. FIG. 8 shows a device with quite limited, discrete adjustment settings, wherein the upper and lower obstruction elements can be adjusted via tracks 120, 140, and the adjustment secured by cotter pins or the like through holes 124, 148, respectively. These limited adjustment settings grant the patient little relief while his/her mandible is thrust forward the distance of the discrete adjustment required by the MARA device, as, for example, adjustment settings spaced 4–5 mm apart. It would be advantageous to provide an intraoral appliance that has a wide range of incremental and continuous adjustment settings, enabling smaller adjustment steps for the ease of the patient than are capable through use of the MARA device.

Since the MARA device has such limited adjustment settings, the device is subjected to enormous forces generated by the jaw muscles as they fight against the forward moving forces dictated by it. Therefore, the MARA device must be fabricated from sufficiently strong materials, or a large amount of material, so as not to break apart in the patient's mouth. As opposed to the MARA device, if a device had continuous adjustment settings so the forces borne by the device were less than those sustained by the MARA device (because the lower jaw is repeatedly moved forward only slightly), such an appliance could then be manufactured from less material or lighter weight material than the MARA device. A lighter appliance would aid in overall patient comfort, and lower costs of manufacturing such an appliance.

Not only do the forces borne by the MARA device necessitate a heavy construction, but they also typically compel the MARA device be secured to the patient's teeth via steel crowns placed on the teeth. Although bands are a preferred mounting assemblies for an intraoral appliance, bands cannot hold up to the above-described forces encountered by the MARA device. "[There are] breakage problems associated with using bands to fabricate the MARA . . . ." CMM, page 16, note. Crowns are the most intrusive type of mounting assemblies for the patient because they are harder to fit than bands, and decay can form under the crowns that would not be reachable by the clinician. Such decay is rarely associated with band use.

Additionally, adjusting the MARA device as shown in FIG. 8 of Eckhart et al. '891 patent only can be done by a dentist or like professional. Another improvement over the Eckhart et al. device would be an appliance designed to be easy to adjust, that if allowed by the dentist, the patient and/or a parent could adjust it without incurring the cost of numerous return trips to the dentist's office for adjustment.

It would also be advantageous to provide an intraoral appliance that can be adjusted by hand, with or without the need of specialized tools. Adjusting the MARA device can require removal of cotter pins, ligature wire and the like, which removal typically requires dental tools.

Further, use of the MARA can irritate the cheeks of the patient. "If the patient's maxillary arch is too narrow, the upper elbows on the MARA will be unable to hang buccally to the mandibular crowns without excessive buccal flaring, which causes . . . cheek irritation." CMM, page 12, note. Thus, an intraoral device incorporating cheek shields to protect the patient's cheeks from irritation would be beneficial.

Thus, it can be seen that there is a need for an improved growth appliance and method to correct malocclusions and the like by deterring an uncorrected bite, yet maintaining a corrected bite, a corrected bite being defined by the intraoral appliance.

BRIEF SUMMARY OF THE INVENTION

The present appliance and method function to apply a force within a patient's mouth that urges one jaw to move relative to the other jaw, generally along his/her normal growth axis, in order to correct the patient's malocclusion. Briefly described, the present invention is directed to an appliance and method for assisting a patient in maintaining a forward-moving force on the patient's mandibular jaw to correct a Class II malocclusion.

The present appliance comprises an adjustment assembly and a placement assembly. The adjustment assembly is mounted to a tooth of the maxilla, and the placement assembly is mounted to a corresponding tooth of the mandible. In this manner, upon jaw closure, the assemblies are in generally vertical alignment. The adjustment assembly cooperates with the placement assembly when the jaws are drawn together, providing the above-mentioned force to the jaws in order to correct the patient's malocclusion. The amount of forward positioning of the lower jaw relative to the upper jaw is finely adjustable through the adjustment assembly. The placement assembly insures that the proper forward positioning of the mandible is maintained when the jaws are closed.

The adjustment assembly includes a first tooth attachment for mounting the adjustment assembly to a tooth on the maxillary jaw, an adjusting mechanism to lengthen or shorten the distance of forward positioning imparted to the patient's mandibular jaw, an abutment member to preserve the proper forward-moving force once the patient's jaws are properly closed, and an inhibiting member that inhibits the patient from closing his/her mouth unless the jaws are "properly seated" relative to one another as defined by the appliance settings. It should be noted that the terms "properly seated" and "corrected bite" herein can mean a relationship between the jaws that changes with the adjustment of the appliance. That is, these terms do not necessarily imply that the patient's malocclusion has been fully corrected, but only that the jaws are properly seated relative to the appliance settings. As such, the appliance can be readjusted, to once again move the lower jaw forward, slowly correcting the overbite. Both since the present appliance is adjustable, and because the malocclusion typically is not completely corrected with only one adjustment setting of the appliance, each "proper seating" or "corrected bite" slowly leads the jaws to a final alignment wherein the malocclusion is fully corrected.

The placement assembly of the present appliance includes a second tooth attachment for mounting the placement assembly to a tooth on the mandibular jaw and a projection element extending from the second tooth attachment. The projection element has a stop end capable both of engagement with the inhibiting member of the adjustment assembly when the patient's jaws are not properly seated, and engagement with the abutment member of the adjustment assembly when the jaws are properly closed. The placement assembly is free of a permanent connection with the adjustment assembly.

The abutment member has an abutment surface, and the inhibiting member has an inhibitory surface. Similarly, the stop end of the projection element incorporates a stoppable surface and a maintainable surface. The abutment member and inhibiting member of the adjustment assembly engage the stop end of the placement assembly at mutually exclusive times.

The adjustment and placement assemblies are mounted on the teeth by the first and second tooth attachments, respectively, so as to place the inhibiting member of the adjustment assembly in generally vertical alignment with the upwardly and buccally extending stop end of the projection element of the placement assembly. This orientation causes the inhibitory surface of the inhibiting member to contact the stoppable surface of the stop end when the patient attempts to close the mandibular and maxillary jaws with the mandibular jaw in an uncorrected position as defined by the appliance settings. In this manner, complete closure of the mandibular and maxillary jaws is prevented unless the mandible is forwardly advanced from the uncorrected position a sufficient amount to enable the inhibiting member to clear the stop end. Once the mandibular jaw is so advanced, the patient may close the maxillary and mandibular jaws and bring the abutment surface of the abutment member into engagement with the maintainable surface of the stop end of the projection element, so as to enable the stop end and the abutment member to assist in maintaining a forward moving force on the patient's mandibular jaw.

The adjusting mechanism of the adjustment assembly essentially provides a continuum of posterior and anterior adjustment settings for the abutment member, which adjustment in turn alters the closed relationship of the jaws. The adjustment of the appliance can be smooth and incremental, that is, the adjustment is non-discrete. The present appliance preferably incorporates two sets of complementary adjustment and placement assemblies; one set on the right side of the mouth and another set on the left side of the mouth. The adjusting mechanism of the adjustment assembly can incorporate opposing body members in communication with each other through an adjustment screw that, upon rotation, finely adjusts the distance separating the opposing body members, in turn changing the anterior-posterior position of the abutment member. In Class II malocclusions, rotation of the adjustment screw of one adjusting mechanism (on the left or right side of the mouth) over time slowly advances that side of the lower jaw forward relative to the upper jaw. The adjustment screw can be advanced more on one side of the mouth than the other for asymmetrical movement in cases where a patient is more Class II on one side of the mouth than on the other.

The adjusting mechanism can further incorporate an anti-torque device to maintain the proper orientation of the adjusting mechanism while the adjustment screw is rotated. Additionally, the screw can be designed so it can be rotated by touch of a finger, removing any need for specialized tools to adjust the appliance.

The present appliance can also be used to correct Class III malocclusions. The adjustment and placement assemblies can be mounted in reverse direction on the maxilla and mandible, respectively. Alternatively, the adjustment assembly can be mounted on a tooth of the mandibular jaw, and the placement assembly can be mounted on a tooth of the maxillary jaw. The present appliance in these orientations can correct underbite.

The present appliance first is fabricated for the patient suffering from a malocclusion, and the appliance then seated in the patient's mouth. The patient is allowed to function with the original malocclusion for a period of time prior to any adjustment of the appliance, so the wearer can become comfortable simply with the weight and placement of the appliance. During this time, the patient's bite is not corrected. After this accommodation phase, the patient, parent or dentist can manipulate the adjusting mechanism of the adjustment assembly to affect the slow forward advance of the abutment member, in turn advancing the one jaw forward relative to the other jaw during proper closure of the jaws. The rate of adjustment can be daily, weekly or longer, as the dentist prescribes.

The present appliance can also incorporate any type of maxillary or mandibular expanders/expansions, for example, a palatal expander, widening the jaws using widening adjustment screws at the same time the malocclusion is addressed. The appliance also can be worn at the same time that orthodontic braces are being used. This ability can speed up typical orthodontic treatment because the clinician can be aligning the teeth at the same time the jaws are being aligned. The present appliance can further include orthodontic archwire tubes/slots for continuous archwire placement.

The present appliance embodies numerous advantages over prior art oral devices. A number of these advantages are described below with specific reference to the Eckhart et al. MARA device. For example, the present appliance can be fabricated from lighter and more comfortable materials than those of the MARA device. The present appliance encounters less force both upon its initial placement in the wearer's mouth, and throughout the use and slight adjustment of the appliance, than those forces sustained by the Eckhart et al. device. Typically, the Eckhart et al. device immediately thrusts the lower jaw forward the entire distance of the overbite, in an attempt to fully correct the malocclusion. Yet, this relatively large shift can place destructive forces on the MARA device immediately upon its fitting in the patient's mouth. Thus, the MARA device is bulky because of its thicker design, or fabricated with costly materials having sufficient strength, in the hopes of keeping the device from breaking in the user's mouth.

In addition to the lighter weight of the present appliance, it can be secured to the patient's jaws with bands, not costly and intrusive crowns. Further, crowns are heavier than bands, which leads to even greater patient discomfort. Instructional pamphlets regarding the Eckhart et al. device (including the CMM) recommend using crowns as opposed to bands to mount the MARA device to the teeth and jaws, because bands can split under the forces typically subjected to the MARA device. Yet bands are preferred over the use of crowns when fitting intraoral devices. The present appliance is preferably mounted to the jaws via bands around the teeth. Many doctors do not like to fit stainless steel crowns because crowns are harder to fit, and decay can form under the crowns that would not be reachable by the clinician, as crowns cover the entire surface of the tooth. These problems do not arise if the appliance is fitted using bands.

Another advantage of the present invention is the addition of an accommodation step in the method of correcting a malocclusion using the present appliance. After the intraoral device is fitted, the wearer goes through an assimilation phase during which time the malocclusion is not addressed. The patient continues to open and close the jaws with the malocclusion. The patient is allowed to accommodate to the new "object" in his/her mouth before any adjustment is made to the appliance. After the patient becomes comfortable with the appliance itself only then is the appliance continually adjusted, which adjustments are barely noticeable, if at all, by the wearer. When a MARA or Herbst device similarly is placed in the mouth, the patient has to immediately force the lower jaw forward several millimeters to occlude posterior teeth. This places more pressure and stress on the muscles of the jaws, which causes tension and soreness for the patient, and can ultimately damage these types of devices. Not only is the patient's bite immediately altered upon fitting of the prior art devices, but the patient must simultaneously overcome the discomfort of the device itself in the mouth.

Additionally, the present appliance provides a range of continuous, fine, incremental adjustment not possible with the Eckhart et al. device.

Another common complaint of the MARA is that it frequently pinches and irritates the inside of the cheeks of the wearer. The present appliance incorporates body members of the adjusting mechanism that act as cheek shields to keep the appliance from irritating the cheeks.

Further, the patient and/or parent, not just the dentist, can manipulate the adjusting mechanism of the present appliance, unlike adjustment of the Eckhart et al. device that requires a dentist visit.

Accordingly, an object of the present invention is to provide an intraoral device and method that enables the patient a sufficient time to accommodate the weight and placement of the new appliance, without any initial adjustment to the patient's jaws.

Another object of the present appliance is to provide an intraoral appliance that has a wide range of continuous adjustment settings, facilitating smooth forward adjustment of the lower jaw that are easily tolerated by the wearer, as opposed to discrete, limited adjustment steps that can be painful for the wearer.

Yet another object of the present invention is the fabrication of an appliance that can be adjusted by the patient and/or parent, not just the dentist.

Another object of the present invention is to enable one to adjust the present appliance without the need of specialized tools, but only with the touch of a finger.

An additional object of the present invention is to provide a lighter weight intraoral appliance than is now presently available, enhancing patient comfort while he/she is wearing the present appliance.

A further object of the present invention is to provide an appliance that can be secured in the patient's mouth via bands, eliminating the various disadvantages associated with mounting an intraoral device by crowns placed on the teeth.

These and other objects, features and advantages of the present invention will become more apparent upon reading the following specification in conjunction with the accompanying drawing figures.

DETAILED DESCRIPTION OF THE PREFERRED EMBODIMENTS

Figure 1:
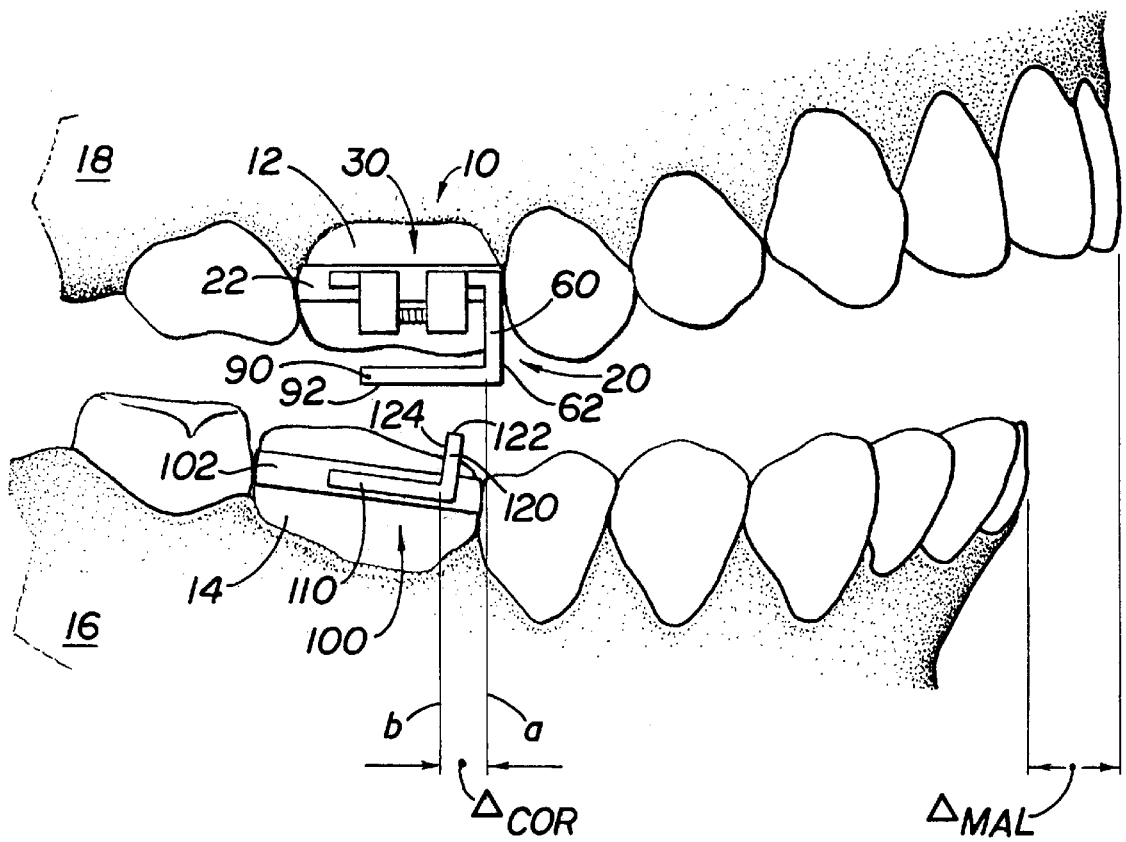
FIG. 1 is a right side view of one embodiment of the present appliance fixed to the jaws of a patient having a malocclusion.

Referring to FIG. 1, the present appliance 10 is shown mounted to the first molars 12, 14 on the right side of a patient having an overbite or overjet, in which the lower jaw 16 is in a retrusive position (the distance of the malocclusion shown as $\Delta_{MAL}$). The present appliance 10 comprises two assemblies, an adjustment assembly 20 mounted on the first molar 12 of the maxillary jaw 18 and a placement assembly 100 mounted on the first molar 14 of the mandibular jaw 16.

The adjustment assembly 20 of the present appliance 10 includes a first tooth attachment 22 that mounts the adjustment assembly 20 to tooth 12 of the maxilla 18, an adjusting mechanism 30 to adjust the amount of correction to the patient's overbite, an abutment member 60 extending from the adjusting mechanism 30 generally both downwardly and normal to the tooth crown, which abutment member 60 maintains the patient's corrected bite, and an inhibiting member 90 extending generally both normal to the abutment member 60 and toward the posterior of the mouth, which inhibiting member 90 deters improper clenching of the jaws.

The placement assembly 100 includes a second tooth attachment 102 that mounts the placement assembly 100 to tooth 14 of the mandible 16, a projection element 110 extending from the tooth attachment 102 generally both parallel to the tooth crown and toward the anterior of the mouth, and a stop end 120 on the projection element 110, the stop end 120 extending in a plane generally normal to the projection element 110 both upwardly and buccally.

With the adjustment assembly 20 fitted to the maxilla, and the placement assembly 100 fitted to the mandible, the present appliance is orientated to best correct a Class II malocclusion. There are two preferable alternatives to reorient the present invention to correct Class III malocclusions. First, preferably, adjustment assembly 20 can be fitted to the maxilla in reverse, and the placement assembly 100 fitted to the mandible likewise in reverse, which orientation best corrects a Class III malocclusion. Other than reversing the orientation of the assemblies 20, 100, another alternative is to fit the adjustment assembly 20 to the mandible, and the placement assembly 100 to the maxilla, without reversing the assemblies.

It will be understood that directional terminology including upwardly and downwardly, and similar upward and downward phraseology, apply for embodiments of the appliance when the adjustment assembly 20 is attached to the maxilla and the placement assembly 100 attached to the mandible when configured to correct a Class II malocclusion. These directional terms would be opposite if the adjustment assembly 20 is attached to the mandible, and the placement assembly 100 attached to the maxilla, as up and down will be reversed. Directional terminology referring to directions in a generally normal plane to those of upward and downward, including interior, posterior and buccal, would remain unchanged if each assembly is switched to the other jaw, but would be opposite in the configuration where the assemblies are reversed, but on the same jaws as is disclosed to correct a Class II malocclusion.

A detailed description of the elements of the present invention follows a brief overview of the rehabilitative functions of the appliance 10. As shown in FIG. 1, the present appliance 10 is adjusted to correct the malocclusion $\Delta_{MAL}$ a corrected distance $\Delta_{COR}$ when the jaws 16, 18 are properly closed as directed by the settings of the appliance 10. Distance $\Delta_{COR}$ is shown less than the entire malocclusion distance $\Delta_{MAL}$ since the present appliance 10 is adjustable, and is designed to fully correct the retrusive position of the mandible in fine steps of adjustment, each corrected adjustment, for example, the distance $\Delta_{COR}$.

The abutment and inhibiting members 60, 90 of the adjustment assembly 20 are designed so as to independently engage the stop end 120 of the placement assembly 100 during proper and improper clenching, respectively. The adjustment and placement assemblies 20, 100 of FIG. 1 are mounted to the jaws so an inhibitory surface 92 of the inhibiting member 90 is in general vertical alignment with a stoppable surface 122 of stop end 120 when the mandibular jaw 16 is improperly closed as defined by the appliance settings. The inhibitory surface 92 is the surface of the inhibiting member 90 facing the mandible 16, and the stoppable surface 122 is the surface of the stop end 120 facing the maxilla 18.

Figure 2:
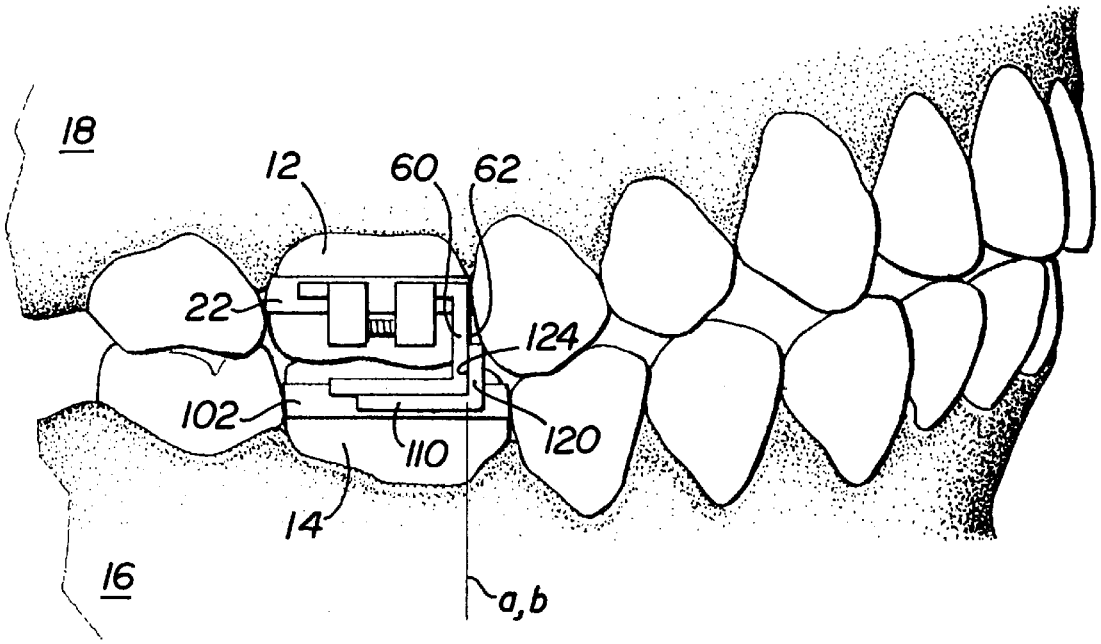
FIG. 2 is a right side view of the patient's jaws of FIG. 1, in a corrected bite with the malocclusion fully corrected.

The above alignment of the assemblies 20, 100 causes the inhibitory surface 92 and stoppable surface 122 to strike one another when the patient attempts to close the mandibular and maxillary jaws 16, 18 with the mandibular jaw 16 in an uncorrected position, thereby preventing complete closure of the mandibular and maxillary jaws 16, 18. However, once the mandibular jaw 16 is advanced in a forward direction from its uncorrected position sufficient to enable the stop end 120 to clear the inhibiting member 90, as shown in FIG. 2, the patient may close the maxillary and mandibular jaws 16, 18 and bring a maintainable surface 124 of stop end 120 into contact with an abutment surface 62 of the abutment member 60. The maintainable surface 124 is the posteriorly-facing surface of the stop end 120, and the abutment surface 62 is the anteriorly-facing surface of the abutment member 60.

During proper closure of the jaws 16, 18 as defined by the appliance settings, distance $\Delta_{COR}$ becomes zero because the lower jaw 16 has been adjusted slightly forward relative to the upper jaw 18 the original adjustment distance $\Delta_{COR}$. The position of abutment surface 62 indicated by dashed line a preferably remains fixed through closure of the jaws, while the position of maintainable surface 124 of stop end 120, indicated by dashed line b, advances forward until the lines a and b lie atop one another when the jaws are properly closed. The patient may, of course, properly close the mouth with a combination of jaw movements, wherein lines a and b are both drawn toward each other. Either way, at this point, the mandible 16 is forward relative to the maxilla 18 the original distance $\Delta_{COR}$, and the remaining distance of the malocclusion to be addressed is $\Delta_{MAL}-\Delta_{COR}$. The contact between the maintainable surface 124 of the stop end 120 and the abutment surface 62 of the abutment member 60 during proper closure enables the stop end 120 and abutment member 60 to assist in maintaining a forward moving force on the patient's mandibular jaw 16.

After a period of time during which the patient's bite grows accustomed to the corrected forward movement of the mandible 16 by the distance $\Delta_{COR}$, settings of appliance 10 are again adjusted to bring the abutment member 60 further forward. Activation of the adjusting mechanism 30 moves the abutment member 60 anteriorly, toward the front of the mouth, urging the lower jaw 16 forward another incremental distance in order to close the jaws, further correcting the original overbite distance $\Delta_{MAL}$. Assuming the appliance were again adjusted a distance $\Delta_{COR}$, the remaining distance of overbite will be $\Delta_{MAL}-2\Delta_{COR}$. Each time the appliance 10 is adjusted, the position of dashed line a is moved some distance forward, indicating adjustment of the abutment surface 62 forward. Adjustment of the appliance 10 is continued over time until the mandible 16 has been slowly moved forward a total distance $\Delta_{MAL}$. Such a final adjustment is illustrated in FIG. 2. The jaws 16, 18 are shown closed, in correct, final alignment.

Figure 3:
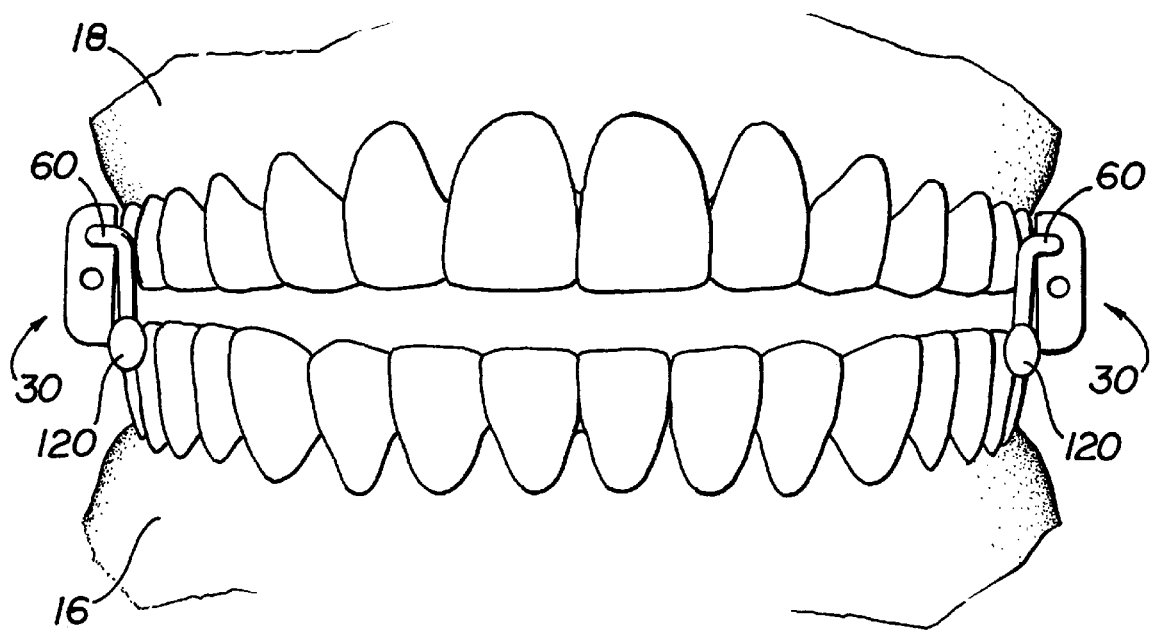
FIG. 3 is a front view of the present appliance incorporating complementary left and right adjustment and placement assemblies.

Preferably, the appliance 10 is mounted on the first molars 12, 14 of the maxillary and mandibular jaws 18, 16, respectively, although depending upon the particular patient and condition being treated, other teeth may be used instead. The appliance 10 generally includes complementary assemblies positioned on the opposite side of a patient's jaws 16, 18. For example, referring to FIGS. 1 and 2, in addition to the assemblies 20, 100 shown mounted on the right side of the patient's mouth, the patient might have complementary mirror-image assemblies mounted on the first molars positioned on the left side of the patient's mouth, as shown in FIG. 3. The use of complementary right and left side assemblies, connected through, for example, a transpalatal arch, resist rotation of the respective upper or lower teeth. However, depending upon the particular treatment needs of a patient, the appliance may be constructed with assemblies 20, 100 only on a single side of a patient's mouth without complementary assemblies positioned on the opposite side of the mouth.

A detailed description of the components of the present appliance 10 is now presented. The adjustment assembly 20 is shown in FIGS. 1–11. The first tooth attachment 22 of the adjustment assembly 20 secures assembly 20 to a tooth, and preferably includes a band 22 that is anatomically proportioned for proper width for the particular tooth size to which it will wrap around. As shown in FIGS. 1 and 2, band 22 encircles a portion of tooth 12. Band 22 should have accurate gingival contour in order to eliminate time consuming festooning and to allow the band 22 to fit slightly below the marginal ridge of the tooth. Flattened interproximals result in less tooth separation, and broad buccal and lingual surfaces enhance retention and allow flexibility in positioning the band 22 more toward the occlusal or gingival, as desired. Preferably the band 22 is malleable by a heat treatment process in order to facilitate the fitting of the band 22.

Figure 4:
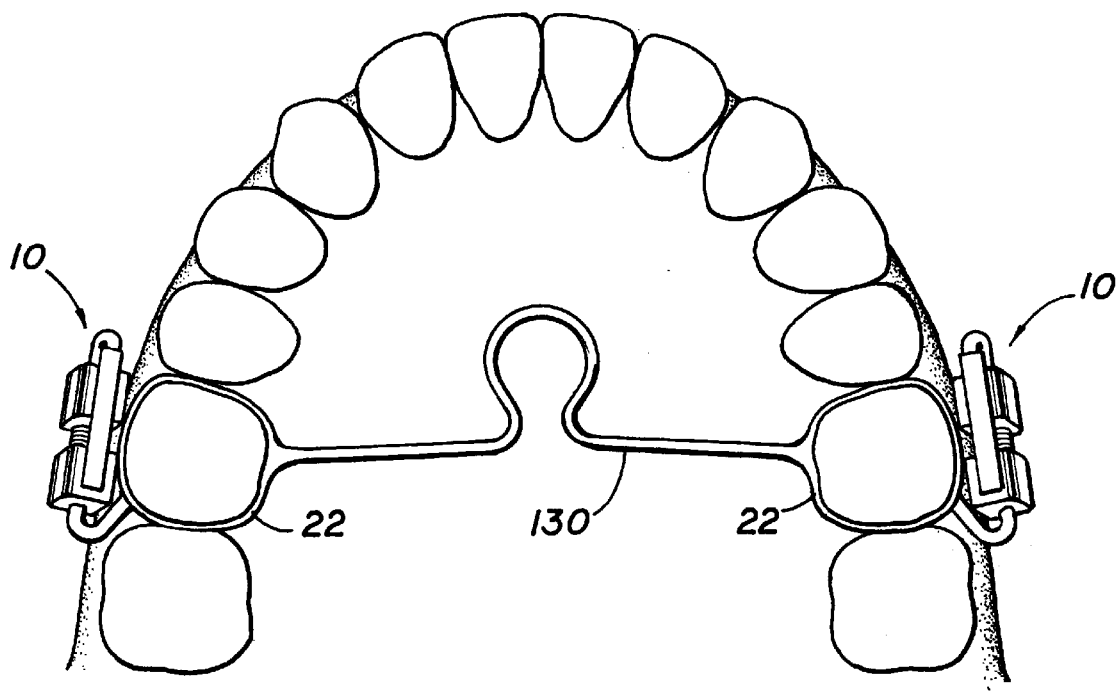
FIG. 4 is a view of a patient's maxilla, wherein the patient is fitted with complementary adjustment assemblies on both sides of the mouth, the adjustment assemblies attached to each other through a transpalatal element.

If the patient is fitted with complementary assemblies on both sides of the mouth, as shown in FIG. 3, both bands 22 should be attached to each other through a transpalatal element 130, for example, a bar, expander or the like, illustrated in FIG. 4. The transpalatal element 130 hinders the molars from orthodontically rotating due to the force/moment being exerted buccal to the molars' centers of rotation.

In another embodiment, first tooth attachment 22 can include a stainless steel veneer crown (not shown), covering the crown of tooth 12 in place of a band.

Figure 5:
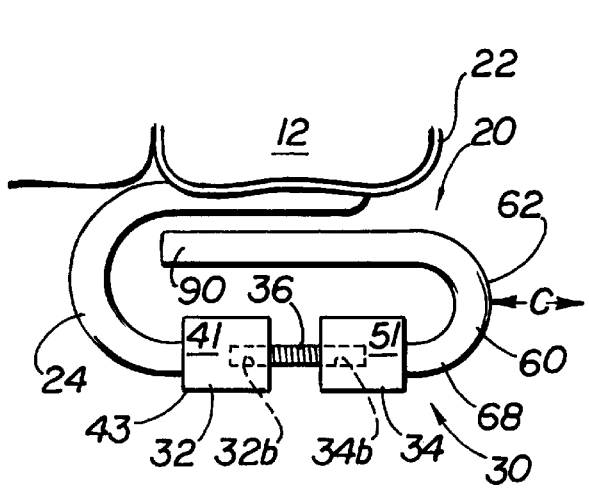
FIG. 5 is a top view of one embodiment of the adjustment assembly of the present appliance.

The first tooth attachment 22 thus secures the adjustment assembly 20 to the patient's upper jaw 18. FIG. 5 illustrates a top view of adjustment assembly 20 according to a preferred embodiment. Extending from band 22 is buccal arm 24. The first tooth attachment 22 further incorporates buccal arm 24 in order to position the adjusting mechanism 30, abutment member 60 and inhibiting member 90 buccally away from tooth 12, so the adjustment assembly 20 will not interfere with the patient's corrected bite, and will act as a check shield.

The adjusting mechanism 30 of adjustment assembly 20 is secured at one end to buccal arm 24, and at the other end to abutment member 60. The adjusting mechanism 30 is designed to adjust the posterior-anterior position of abutment surface 62 as indicated by double arrow C in FIGS. 5 and 6. Adjusting mechanism 30 preferably comprises two opposing body members 32, 34 in communication with each other through an adjustment screw 36 that, upon rotation, finely adjusts the distance separating the opposing body members 32, 34, in turn altering the posterior-anterior position of the abutment member 60. During normal use of the present appliance, the adjusting mechanism 30 moves the abutment member 60 forward in order to correct the retrusive lower jaw. Yet, when appropriate, the adjusting mechanism 30 can move the abutment member 60 posteriorly.

As shown in FIGS. 5–8, body member 32 has a top surface 41, a bottom surface 42, a posterior surface 43, an anterior surface 44, and a buccal surface 45. Similarly, body member 34 has a top surface 51, a bottom surface 52, a posterior surface 53, an anterior surface 54, and a buccal surface 55. Buccal arm 24 of the first tooth attachment 22 is attached to the posterior surface 43 of body member 32; as such, the position of body member 32 is fixed throughout the adjustment of the appliance 10 since buccal arm 24 is in turn fixed to first attachment 22, itself secured to tooth 12. Therefore, rotation of screw 36 advances or retreats the position of body member 34.

Figure 6:
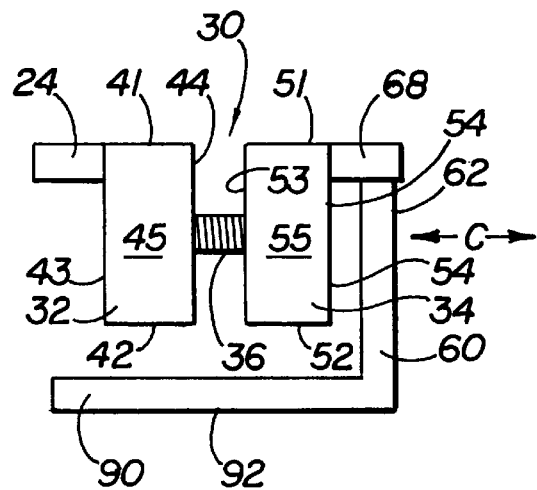
FIG. 6 is a side view of the adjustment assembly of FIG. 5.
Figure 7:
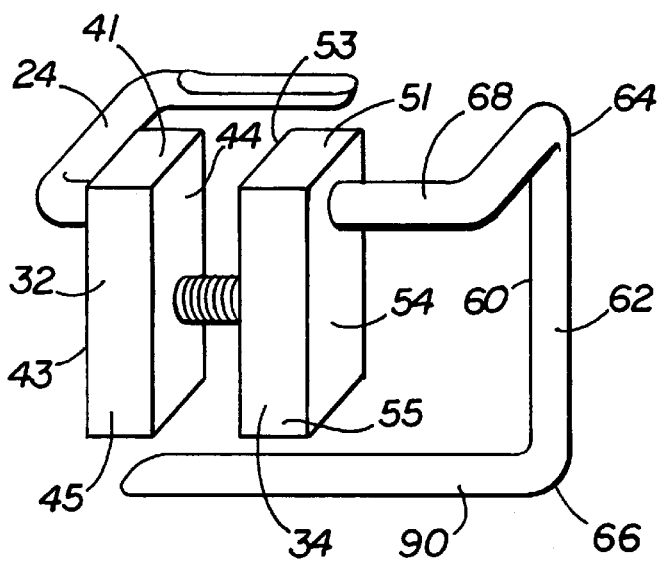
FIG. 7 is a perspective view of the adjustment assembly of FIG. 5.
Figure 8:
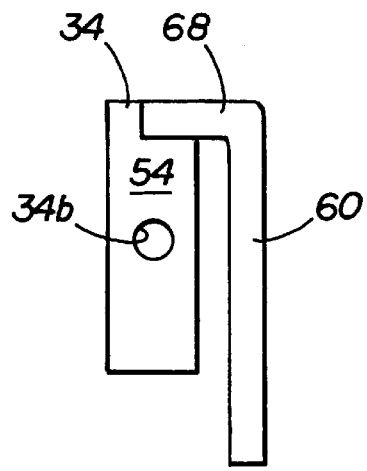
FIG. 8 is a front view of the adjustment assembly of FIG. 5.

The adjustment screw 36 engages each body member 32, 34 through threaded bores 32b, 34b in the central region of each body member, through the anterior surface 44 of body member 32, and the posterior surface 53 of body member 34. The end sections of adjustment screw 36 are threaded in a reverse orientation from one another, designed to mesh with the respective bores 32b, 34b in body members 32, 34, in a manner well known in the art. One or both threaded bores 32b, 34b may terminate in the body member, or may extend through the body member, through either the posterior surface 43 of body member 32 or the anterior surface 54 of body member 34. FIG. 8 illustrates bore 34b extending through body member 34. Since threaded bore 32b can extend through the body member 32, buccal arm 24 preferably attaches to the posterior surface 43 of body member 32 distal from the location where bore 32b would exit posterior surface 43. For example, FIGS. 5–7 show buccal arm 24 attached to posterior surface 43 nearer top surface 41 than is bore 32b.

Figure 9:
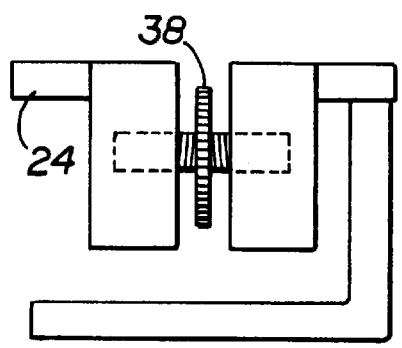
FIG. 9 is a side view of another embodiment of an adjustment assembly of the present invention having an actuating ring.

In order to facilitate the rotation of adjustment screw 36 without the need of a specialized tool, the central section of screw 36 can incorporate an actuating ring 38, shown in FIG. 9. Screw actuating ring 38 is oriented coaxially with screw 36. Preferably, ring 38 does not extend buccally past body members 32, 34, so the ring 38 does not interfere with the patient's cheek. In operation, actuating ring 38 is rotated through an arc about screw 36, thereby rotating adjustment screw 36. The oppositely threaded configuration of the ends of screw 36 causes body member 34 to be brought nearer to or further away from body member 32, depending on the direction of rotation of the ring 38. For example, positive rotation of screw actuating ring 38 causes opposed body members 32, 34 to be drawn closer together, while negative rotation of actuating ring 38 results in diminishing the distance between the body members 32, 34.

In another embodiment, adjustment screen 36 can be adjusted at one of its ends, and not necessarily inbetween body members 32, 34. Referring again to FIG. 8, screw 36 can be rotated through bore 34b.

Figure 10:
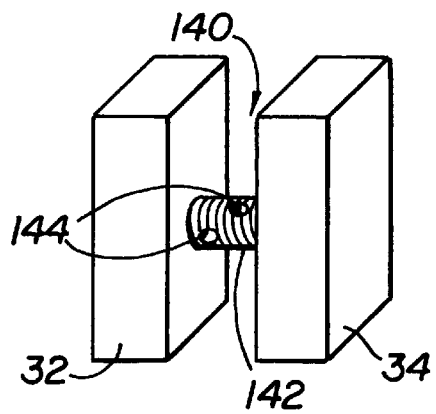
FIG. 10 is a perspective view of one embodiment of the adjusting mechanism of the present invention incorporating an adjustment shielding device.

Alternatively, if the patient cannot be trusted with adjustment of the appliance, the adjusting mechanism 30 can be fitted with an adjustment shielding device 140, thus shielding adjustment of the appliance from anyone without, for example, a specialized tool. One embodiment of an adjustment shielding device is shown in FIG. 10, and includes a screw jacket or casing 142 that envelops an adjustment screw 36. The jacket 142 can incorporate periodic keyways 144, which keyways 144 enable only a specialized tool, like an Allen wrench, to fit within and thus rotate the screw jacket 142 via leverage. The shielding device can also incorporate a screw 36 with one end having an appropriate keyway, so the screw 36 can only be adjusted at one end with a specialized tool. (For example, using the described adjusting of screw 36 with reference to FIG. 8.)

Figure 14:
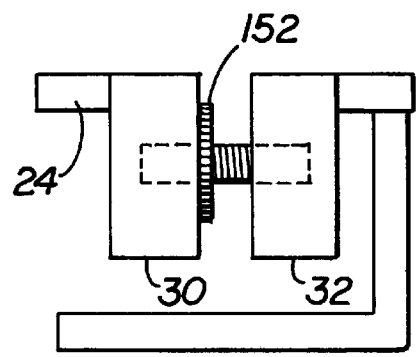
FIG. 14 is a side view of an adjustment assembly having a locking device.

The adjusting mechanism 30 can further incorporate an adjustment locking device 150 as shown in FIG. 14, that prevents the accidental retreat of the adjustment distance between the body members 32, 34. Such an adjustment locking device 150 would also prevent the patient from self-adjusting the appliance in a direction opposite from correction of the malocclusion. Adjustment locking device 150 is shown as a locking ring 152 which is continually adjusted to abut body member 32 or 34 so as to inhibit reverse rotation of screw 36.

Figure 11:
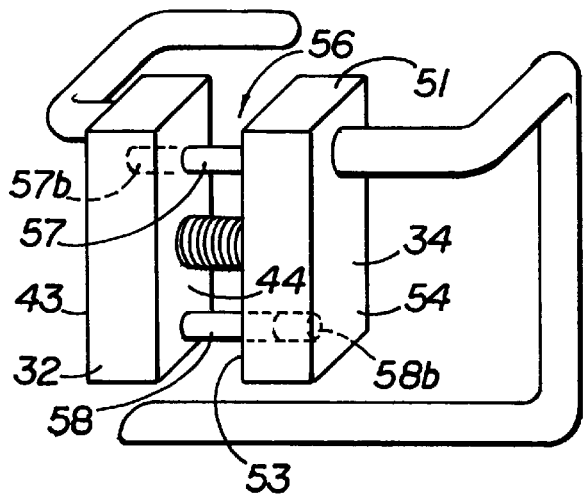
FIG. 11 is perspective view of an adjustment assembly according to the present invention having an anti-torque device.

Adjusting mechanism 30 can further comprise an anti-torque device 56 to maintain the integrity of the adjusting mechanism 30 while the adjustment screw 36 is rotated. FIG. 11 shows anti-torque device 56 including two rods 57, 58. Rods 57, 58 stabilize the body members 32, 34 as the distance between them is incrementally expanded or retracted. The rods 57, 58 also act to provide structural integrity to the appliance 10. In one embodiment of anti-torque device 56, rod 57 is secured at one end to the posterior surface 53 of body member 34, and extends through a bore 57b in body member 32. The opposing end of rod 57 can slide in bore 57b, and either terminates within bore 57b, or extends through body member 32, exiting the posterior surface 43 of body member 32, should rod 57 and bore 57b be so configured. Similarly, rod 58 is secured at one end to the anterior surface 44 of body member 32, and extends through a bore 58b in body member 34. The opposing end of rod 58 can slide in bore 58b, and either terminates within bore 58b, or extends through body member 34, exiting the anterior surface 54 of body member 34 should bore 58b be so configured.

Alternatively, anti-torque device 56 can comprise only one rod, or more than two rods.

Body members 32, 34 preferably incorporate rounded edges and rounded buccal surfaces 45, 55 respectively, which edges and surfaces present comfortable edges and surfaces when engaged with the patient's cheek, these surfaces 45, 55 providing cheek shields for the appliance 10.

The abutment member 60 of the adjustment assembly 20 includes an abutment surface 62 extending in a generally gingival-occlusal direction between a gingival extremity 64 and an occlusal extremity 66, as shown in FIG. 7. The abutment member 60 preferably includes an extension element 68 (FIGS. 5–8) in order to position the abutment surface 62 forward the adjusting mechanism 30. The extension element 68 projects from the anterior surface 54 of body member 34. The abutment member 60 is secured at one end to body member 34 by extension element 68, and at the other end to inhibiting member 90. Since threaded bore 34b and/or 58b can extend through the body member 34, extension element 68 preferably attaches to the anterior surface 54 of body member 34 gingival from the location where bores 34b/58b would exit anterior surface 54. For example, FIGS. 6–9 and 11 show abutment member 60 attached to anterior surface 54 nearer top surface 51, than is either bore 34b or 58b.

In a preferred embodiment, abutment member 60 forms an upside-down L-shaped member 60, which positions inhibiting member 90 distal from the patient's cheek relative to the adjusting mechanism 30. In this configuration, body members 32, 34 are the buccal-most elements of the appliance 10, providing cheek shielding surfaces 45, 55. FIGS. 1 and 2 illustrate abutment surface 62 extending generally normal to jaw 18, presenting a surface that will abut maintainable surface 124 of stop end 120 of projection element 110 upon proper closure of the jaws 16, 18.

The adjustment assembly 20 further comprises inhibiting member 90 extending generally posteriorly and normal from the abutment member 60 from the occlusal extremity 66 of the abutment surface 62. Inhibiting member 90 includes inhibitory surface 92 that strikes the stoppable surface 122 of placement assembly 100 when the patient attempts to close the mandibular and maxillary jaws 16, 18 with the mandibular jaw 16 in an uncorrected position, thereby preventing complete closure of the mandibular and maxillary jaws 16, 18.

Figure 12:
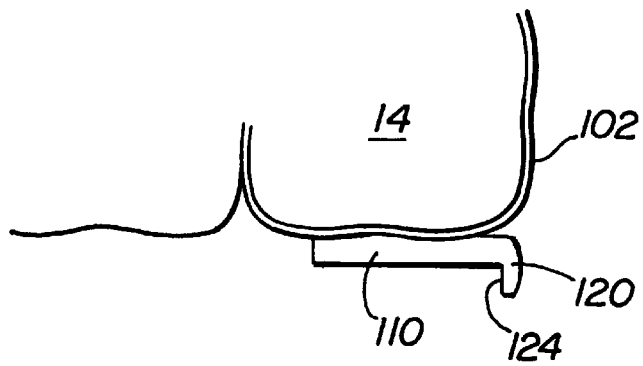
FIG. 12 is top view of a placement assembly of the present invention.

Referring now to placement assembly 100, as shown in FIG. 12, the second tooth attachment 102 of the placement assembly 100 preferably includes a band 102 that is anatomically proportioned for proper width for the particular tooth size, similar to band 22 of adjustment assembly 20. Alternatively, second tooth attachment 102 can include a stainless steel veneer crown 104, covering the crown of tooth 14.

The placement assembly further comprises a projection element 110 extending anteriorly from the second tooth attachment 102. The posterior end of the projection element 110 is fixed to the second tooth attachment 102 by known means.

Figure 13:
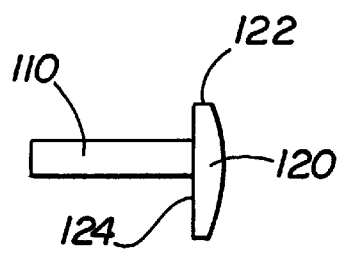
FIG. 13 is a side view of the placement assembly of FIG. 12.

A stop end 120 is provided at the anterior end of the projection element, having portions extending both upwardly and buccally. FIGS. 3, 12 and 13. An inhibitory surface 122 tops the upwardly extending portion of stop end 120, and the posterior surface of stop end 120 includes a maintainable surface 124. When the jaws are properly closed, the abutment surface 62 engages the maintainable surface 124 and maintains the jaws in a corrected bite.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. An intraoral appliance for the mouth of a patient with a malocclusion of the maxillary and mandibular jaws, the malocclusion incorporating an offset distance of one of said jaws relative the other jaw, the maxilla and mandible having teeth with crowns, the mouth having an anterior and posterior end and a left and right side, said appliance capable of deterring improper closure of the jaws and maintaining proper closure of the jaws, said appliance comprising:
   a. an adjustment assembly having a first tooth attachment capable of mounting said adjustment assembly to a tooth of one of the maxilla or mandible, an adjusting mechanism extending from said first tooth attachment capable of defining proper and improper closure of the jaws, said adjusting mechanism further capable of adjusting the amount of offset distance between the maxilla and mandible during proper closure of the jaws, said adjusting mechanism capable of providing incremental and continuous adjustment to the offset distance, an abutment member extending from said adjusting mechanism, said abutment member capable of maintaining proper closure of the jaws, and an inhibiting member extending from said abutment member, said inhibiting member capable of deterring improper closure of the jaws; and
   b. a placement assembly having a second tooth attachment capable of mounting said placement assembly to a tooth of the other of the maxilla or mandible, a projection element extending from said second tooth attachment, and a stop end on said projection element; said adjustment and placement assemblies mounted on respective teeth by said first and second tooth attachments, respectively, so as to place said inhibiting member of said adjustment assembly in alignment with said stop end of said projection element of said placement assembly, said alignment enabling said inhibiting member to contact said stop end during improper closure of the jaws, and said alignment enabling said abutment member to engage said stop end of said projection element during proper closure of the jaws.

2. The intraoral appliance of claim 1, wherein said first tooth attachment comprises a dental band.

3. The intraoral appliance of claim 2, wherein said second tooth attachment comprises a dental band.

4. The intraoral appliance of claim 1, wherein said adjusting mechanism incorporates an adjustment shielding device capable of selectively shielding adjustment of said appliance from the patient.

5. The intraoral appliance of claim 1, wherein said adjusting mechanism incorporates an adjustment locking device capable of preventing the accidental adjustment of said appliance.

6. The intraoral appliance of claim 1, wherein said adjusting mechanism comprises two opposing body members, a first and a second body member, said body members separated by a distance, said first body member connected to said first tooth attachment, said second body member attached to said abutment member, said body members in communication with each other through an adjustment screw that, upon rotation, is capable of adjusting the distance separating the opposing body members, in turn altering the posterior-anterior position of said abutment member.

7. The intraoral device of claim 6, wherein said adjustment screw has an actuating ring oriented coaxially with said adjustment screw.

8. The intraoral device of claim 7, wherein said adjusting mechanism further incorporates an anti-torque device capable of stabilizing said body members upon rotation of said adjusting screw.

9. The intraoral device of claim 8, wherein said anti-torque device comprises a rod extending from one said body member and through a portion of said other body member.

10. An intraoral appliance for the mouth of a patient with a malocclusion of the maxillary and mandibular jaws, the malocclusion incorporating an offset distance of one of said jaws relative the other jaw, the maxilla and mandible having teeth with crowns, the mouth having an anterior and posterior end and a left and right side, said appliance capable of deterring improper closure of the jaws and maintaining proper closure of the jaws, said appliance comprising:
   a. an adjustment assembly having a first tooth attachment capable of mounting said adjustment assembly to a tooth of one of the maxilla or mandible, an adjusting mechanism extending from said first tooth attachment capable of defining proper and improper closure of the jaws, said adjusting mechanism further capable of adjusting the amount of offset distance between the maxilla and mandible during proper closure of the jaws, said adjusting mechanism capable of providing incremental and continuous adjustment to the offset distance, an abutment member extending from said adjusting mechanism generally both downwardly and normal to the tooth crown, said abutment member having an abutment surface, said abutment member capable of maintaining proper closure of the jaws, and an inhibiting member extending generally both normal from said abutment member and toward the posterior end of the mouth, said inhibiting member having an inhibitory surface, said inhibiting member capable of deterring improper closure of the jaws; and b. a placement assembly having a second tooth attachment capable of mounting said placement assembly to a tooth of the other of the maxilla or mandible, a projection element extending from said second tooth attachment generally both parallel to the tooth crown and toward the anterior end of the mouth, and a stop end on said projection element, said stop end having a stoppable surface and a maintainable surface, said stop end extending both upwardly and buccally in a plane generally normal to said projection element;

said adjustment and placement assemblies mounted on respective teeth by said first and second tooth attachments, respectively, so as to place said inhibiting member of said adjustment assembly in alignment with said upwardly and buccally extending stop end of said projection element of said placement assembly, said alignment enabling said inhibitory surface of said inhibiting member to contact said stoppable surface of said stop end during improper closure of the jaws, and said alignment enabling said abutment surface of said abutment member to engage said maintainable surface of said stop end of said projection element during proper closure of the jaws.

11. The intraoral appliance of claim 10, said appliance comprising two sets of complementary adjustment and placement assemblies, one set located on the right side of the mouth, and a second set on the left side of the mouth.

12. The intraoral appliance of claim 11, further comprising a transpalatal element in communication between said first tooth attachments of each said complementary adjustment assemblies.

13. The intraoral appliance of claim 11, further comprising a buccal arm, said buccal arm extending from said first tooth attachment to said adjusting mechanism, said buccal arm capable of positioning said adjusting mechanism, abutment member and inhibiting member from interfering with the proper closure of the jaws.

14. The intraoral appliance of claim 11, wherein said adjusting mechanism comprises two opposing body members, a first and a second body member, said body members separated by a distance, said first body member connected to said first tooth attachment, said second body member attached to said abutment member, said body members in communication with each other through an adjustment screw that, upon rotation, is capable of adjusting the distance separating the opposing body members, in turn altering the posterior-anterior position of said abutment member.

15. The intraoral device of claim 14, wherein said adjustment screw has an actuating ring oriented coaxially with said adjustment screw.

16. The intraoral appliance of claim 14, wherein said adjusting mechanism incorporates an adjustment shielding device capable of selectively shielding adjustment of said appliance from the patient, said adjustment shielding devices enveloping said adjustment screw.

17. The intraoral appliance of claim 14, wherein said adjusting mechanism incorporates an adjustment locking device capable of preventing the accidental adjustment of said appliance.

18. The intraoral device of claim 14, wherein said adjusting mechanism further incorporates an anti-torque device capable of stabilizing said body members upon rotation of said adjusting screw.

19. The intraoral device of claim 18, wherein said anti-torque device comprises a rod extending from one said body member and through a portion of said other body member.

20. The intraoral device of claim 14, wherein said body members incorporate rounded edges and surfaces, said body members presenting cheek shields to the cheeks of the mouth.

21. The intraoral device of claim 10, wherein said abutment member incorporates an extension element extending from said second body member, said extension element capable of positioning said abutment surface anterior said second body member.

22. A method of correcting the bite of a patient with a malocclusion of the maxillary and mandibular jaws, the bite of the patient including a proper and improper closure of the jaws, the malocclusion incorporating an offset distance of one of said jaws relative the other jaw, the maxilla and mandible having teeth with crowns, the mouth having an anterior and posterior end and a left and right side, said method comprising the steps of:

a. mounting an adjustment assembly to a tooth of one of the maxilla or mandible by a first tooth attachment, said adjustment assembly being provided with an adjusting mechanism extending from said first tooth attachment capable of defining proper and improper closure of the jaws, said adjusting mechanism further capable of adjusting the amount of offset distance between the maxilla and mandible during proper closure of the jaws, said adjusting mechanism capable of providing incremental and continuous adjustment to the offset distance, an abutment member extending from said adjusting mechanism, said abutment member having an abutment surface, said abutment member capable of maintaining proper closure of the jaws, and an inhibiting member extending from said abutment member, said inhibiting member having an inhibitory surface, said inhibiting member capable of deterring improper closure of the jaws; and b. mounting a placement assembly to a tooth of the other of the maxilla or mandible by a second tooth attachment, said placement assembly being provided with a projection element extending from said second tooth attachment, and a stop end on said projection element, said stop end having a stoppable surface and a maintainable surface;

said adjustment and placement assemblies mounted on respective teeth by said first and second tooth attachments, respectively, so as to place said inhibiting member of said adjustment assembly in alignment with said stop end of said projection element of said placement assembly, said alignment enabling said inhibitory surface of said inhibiting member to contact said stoppable surface of said stop end during improper closure of the jaws, and said alignment enabling said abutment surface of said abutment member to engage said maintainable surface of said stop end of said projection element during proper closure of the jaws.

23. The method of correcting the bite of a patient with a malocclusion of the maxillary and mandibular jaws according to claim 22, further including an accommodation step before the bite of the patient is corrected, said accommodation step providing the patient time to become comfortable simply with the weight and placement of said assemblies in the mouth, before the malocclusion is addressed.

* * * * *

UNITED STATES PATENT AND TRADEMARK OFFICE
CERTIFICATE OF CORRECTION

PATENT NO : 6,099,304
DATED : August 8, 2000
INVENTOR(S): David B. Carter

It is certified that error appears in the above-identified patent and that said Letters Patent are hereby corrected as shown below:

Title page, item [75] should read--
 Inventor: David B. Carter --

Signed and Sealed this

Twenty-second Day of May, 2001

Attest:

NICHOLAS P. GODICI

Attesting Officer

Acting Director of the United States Patent and Trademark Office